United States Patent [19]

Trescony et al.

[11] Patent Number: 5,246,451
[45] Date of Patent: Sep. 21, 1993

[54] VASCULAR PROSTHESIS AND METHOD

[75] Inventors: Paul V. Trescony, Robbinsdale, Minn.; Patrick Cahalan, Stein, Netherlands; Kenneth Keeney, Forest Lake, Minn.

[73] Assignee: Medtronic, Inc., Minneapolis, Minn.

[21] Appl. No.: 693,753

[22] Filed: Apr. 30, 1991

[51] Int. Cl.$^5$ .............................................. A61F 2/06
[52] U.S. Cl. ................................... 623/1; 427/2; 427/490; 427/539; 435/240.23
[58] Field of Search ............... 427/2, 40, 41, 490, 427/538, 536, 539; 623/1; 435/240.23

[56] References Cited

U.S. PATENT DOCUMENTS

| | | | |
|---|---|---|---|
| 4,312,575 | 1/1982 | Peyman et al. | 427/490 |
| 4,613,517 | 9/1986 | Williams et al. | 427/2 |
| 4,632,842 | 12/1986 | Karwoski et al. | 427/2 |
| 4,652,263 | 3/1987 | Herweck et al. | 623/1 |
| 4,656,083 | 4/1987 | Hoffman et al. | 427/41 |
| 4,718,907 | 1/1988 | Karwoski et al. | 623/12 |
| 4,919,659 | 4/1990 | Horbett et al. | 623/1 |
| 4,927,676 | 5/1990 | Williams et al. | 427/2 |
| 4,948,628 | 8/1990 | Montgomery et al. | 427/41 |
| 4,994,298 | 2/1991 | Yasuda | 427/41 |
| 5,034,265 | 7/1991 | Hoffman et al. | 427/490 |
| 5,055,316 | 10/1991 | Hoffman et al. | 427/40 |

FOREIGN PATENT DOCUMENTS

| | | | |
|---|---|---|---|
| 3326376 | 1/1985 | Fed. Rep. of Germany | 427/490 |
| 61-070080 | 4/1986 | Japan | 427/490 |
| 3-014677 | 1/1991 | Japan | 427/490 |
| 8910377 | 11/1989 | World Int. Prop. O. | |

OTHER PUBLICATIONS

Morosoff, N. et al. A Study of Electroless Glow Discharge as a Means of Modifying the Surface of Polymers, National Technical Information Service publication PB-293570, Feb. 1979, pp. 19-20.

Morosoff, et al, A Study of Electroless Glow Discharge as a Means of Modifying the Surface of Polymers, National Technical Information Service publication PB80-212715, 1980, pp. 142-133. (no month available).

Yasuda, H. et al, Biomedical Applications of Plasma Polymerization and Plasma Treatment of Polymer Surfaces, Biomaterials 1982, vol. 3 Apr. pp. 69-70.

Gombotz, W. et al, Gas-Discharge Techniques for Biomaterial Modification, CRC Critical Reviews in Biocompatability, vol. 4, Issue 1 (1988) pp. 14-24 (no month available).

Sharma, C. et al. Inhibition of Platelet Adhesion to Glow Discharge Modified Surfaces, Journal of Biomaterials Application, vol. 1, Apr., 1987 pp. 537-539.

Yeh, Y. S. et al., Blood Compatibility of Surfaces Modified by Plasma Polymerization, Journal of Biomedical Materials Research, vol. 22, 795-818 (1988) (no month available).

Kaplan, S. L. et al., Medical Polymers and Plasma Technology, Plasma Science, Inc., 8/88 No. 5 Oct., 1988.

(List continued on next page.)

*Primary Examiner*—Shrive Beck
*Assistant Examiner*—Diana L. Dudash
*Attorney, Agent, or Firm*—Daniel W. Latham; Harold R. Patton

[57] ABSTRACT

A vascular graft with improved endothelial cell adhesion can be achieved on a fluoropolymer surface of a vascular graft by treating the fluoropolymer with a plasma in the presence of a non-polymerizing gas capable of providing the fluoropolymer with anionic groups and binding a protein to the treated fluoropolymer. In a preferred embodiment, the fluoropolymer surface is a plasma deposited fluoropolymer. Also in a preferred embodiment, autologous endothelial cells are seeded onto the vascular graft prior to implantation of the vascular graft in the human body.

5 Claims, 3 Drawing Sheets

OTHER PUBLICATIONS

Chinn, J. A. et al., Enhancement of Seven Fibronectin Adsorption and the Clonal Plating Efficiencies of Swiss Mouse 3T3 Fibroblast and MM14 Mouse Myoblast Cells on Polymer Substrates Modified by Radiofrequency Plasma Deposition, Journal of Colloid and Interface Science, vol. 127, No. 1, Jan. 1989.

Klein-Soyer, C. et al., Culture of Human Vascular Endothelial Cells on a Positively Charged Polystyrene Surface, Primaria: Comparison with Fibronectin-Coated Tissue Culture Grade Polystyrene, Biomaterials Mar. 1989, v. 10.

Pratt, K. J. et al, Enhanced Adherence of Human Adult Endothelial Cells to Plasma Discharge Modified Polyethylene terephthalate, Journal of Biomedical Materials Research, vol. 23, 1131–1147 (1989). (no month available).

Golander, C-G et al., Characterization of Hydrophobicity Gradients Prepared by Means of Radio Frequency Plasma Discharge 1990 (no month available).

Sipehia, R., The Enhanced Attachment and Growth of Endothelial Cells on Anhydrous Ammonia Gaseous Plasma Modified Surfaces of Polystyrene and Poly (Tetrafluoroethylene). 1990 (no month available).

Ertel, S. I. et al., Radiofrequency Plasma Deposition of Oxygen-containing Films on Polystyrene and Poly (ethylene terephthalate) Substrates Improves Endothelial Cell Growth, Journal of Biomedical Materials Research, vol. 24, 1637–1659 (1990) (no month available).

Tanfani F. et al, Glycidyl Acrylate Plasma Glow Discharged Polymers, Biomaterials 1990, vol. II, Oct.

Dekker, A. et al., Adhesion of Endothelial Cells and Adsorption of Serum Proteins on Gas Plasma-treated Polytetrafluoroethylene, Biomaterials, 1991, vol. 12 Mar.

VASCULAR PROSTHESIS AND METHOD

BACKGROUND OF THE INVENTION

This invention relates to artificial vascular grafts and in particular to vascular grafts made with a fluoropolymer surface.

The autogenous saphenous vein or internal mammary arteries are preferred materials for small-diameter arterial replacement but are not always available or suitable, necessitating the use of a prosthetic graft. A variety of synthetic grafts are available for small diameter arterial replacement but their long-term patency has been less than satisfactory due to intimal hyperplasia and thrombosis.

Autologous endothelial cell seeding can reduce the thrombogenicity of synthetic graft surfaces and is gaining acceptance as a useful adjunct to prosthetic graft implantation. However, vascular graft surfaces tend to be poor substrates for cell adhesion and the fraction of seeded cells which adhere in the time frame dictated by graft implantation procedures is relatively low. Some investigators have pre-coated vascular prostheses with various extracellular matrix proteins in an attempt to improve cell adhesion but the poor binding of many of such proteins to graft material also causes cell adhesion to remain poor.

Plasma discharge, the exposure of biomaterials to a plasma or ionized gas, with the resulting creation of functional groups or surface coatings on a material surface have also been used in the preparation of vascular grafts. For example, in U.S. Pat. No. 4,718,907 vascular prosthesis material is provided with a coating of fluorine-containing polymer on its luminal surfaces having a ratio of fluorine to carbon greater than 1.5 to improve patency of the implanted graft. Also, for example, plasma discharge treatment of some vascular prosthesis material in the presence of some non-polymerizing gases (such as ammonia plasma treatment of polystyrene and polytetrafluoroethylene graft material) have been shown to increase protein binding and endothelial cell adhesion.

However, none of these methods have proven entirely successful in providing a small-diameter vascular graft of synthetic material with good endothelial cell attachment for long term patency.

It is therefore an object of the present invention to provide a vascular graft material with improved binding of extracellular matrix proteins such as fibronectin and laminin.

It is also an object of the present invention to provide a vascular graft material with improved binding of endothelial cells for autologous endothelial cell seeding of prosthetic vascular grafts.

It is also an object of the present invention to provide a small-diameter vascular graft prosthesis having improved prospects for long-term patency.

SUMMARY OF THE INVENTION

These and other objects are accomplished by the vascular graft material and method of the present invention. We have discovered that a vascular graft with improved endothelial cell adhesion can be achieved on a vascular graft having a fluoropolymer surface by treating the fluoropolymer with a plasma in the presence of a non-polymerizing gas capable of providing the fluoropolymer with anionic groups and binding a protein to the treated fluoropolymer. In a preferred embodiment, the fluoropolymer surface is a plasma deposited fluoropolymer. Also in a preferred embodiment, autologous endothelial cells are seeded onto the vascular graft prior to implantation of the vascular graft in the human body.

DETAILED DESCRIPTION OF THE INVENTION

Figure 1:
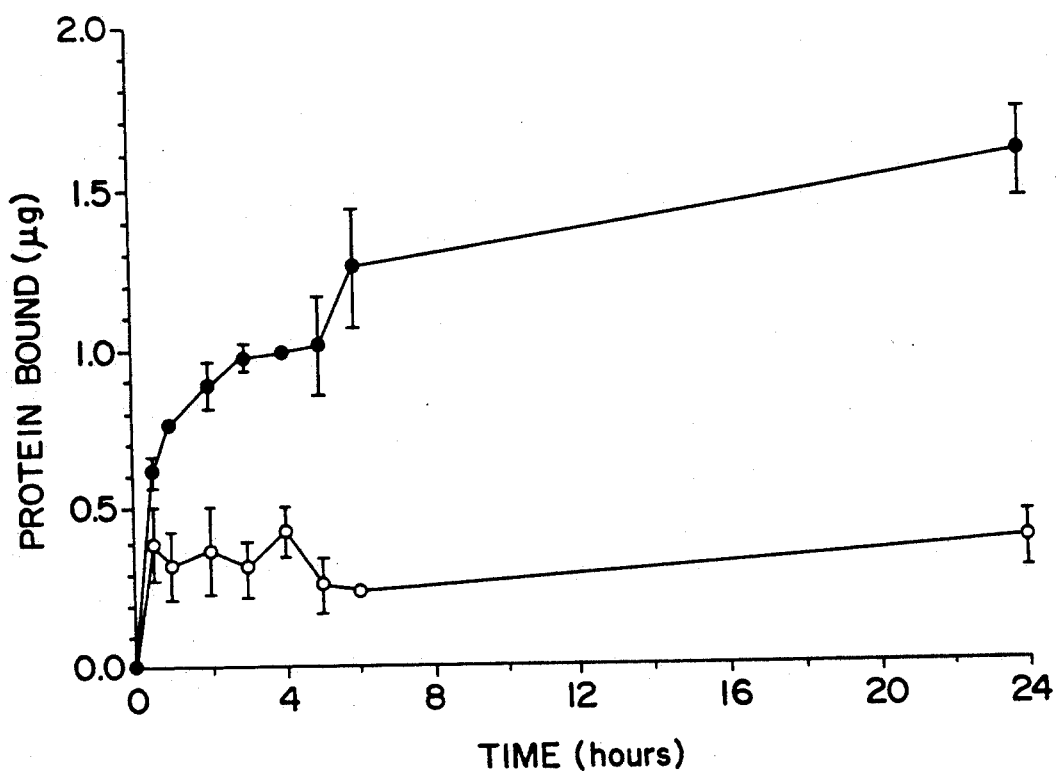
FIG. 1 is a graph showing time-dependent binding of laminin (solid data points) and fibronectin (open data points) to fluoropolymer deposited on vascular graft material according to the prior art.

The vascular graft and method of the present invention provides improved protein binding to vascular grafts and improved potential for endothelial cell adhesion and long term patency over vascular grafts known in the prior art. A fluoropolymer vascular graft surface is first treated by plasma while in contact with a non-polymerizing gas capable of providing anionic groups on the deposited fluoropolymer and then a protein is bound to the anionic fluoropolymer. In a preferred embodiment, the fluoropolymer surface is a plasma deposited fluoropolymer. Also in a preferred embodiment, autologous endothelial cells are seeded onto the vascular graft prior to implantation of the vascular graft in the human body.

The vascular graft of the present invention can be made from any base material capable of plasma treatment according to the present invention. Preferably, however, the base is a material which is substantially biocompatible such as polyesters, polyamides, polyurethanes, polyolefins, polytetrafluoroethylene and the like. For example, a conventional woven vascular graft material of polyethylene teraphthalate can be used. In a preferred embodiment, a microfiber fabric vascular graft woven as taught in U.S. Pat. No. 4,652,263 is used and such teachings are incorporated herein by reference.

The surface which is treated by plasma in the present invention is a fluoropolymer surface. This can include polytetrafluoroethylene (PTFE), fluorinated ethylene propylene and other materials. In a preferred embodiment, the vascular graft base material is subjected to plasma treatment in a polymerizing fluorocarbon gas under conditions which provides a deposited fluoropolymer on the vascular graft base material. For example, a coating can be applied according to U.S. Pat. No. 4,632,842 and/or U.S. Pat. No. 4,718,907 which teachings are hereby incorporated by reference. Generally, a tube made from the desired vascular graft base material is introduced into a tubular glow discharge apparatus, the apparatus is evacuated and a flow of fluorinated gas such as tetrafluoroethylene, hexafluoropropane, or other plasma polymerizable fluorinated hydrocarbon is established within the apparatus. The radio frequency glow discharge is then activated within the apparatus, thereby inducing the deposition of the fluorine-containing polymer onto the base material.

In yet another preferred embodiment, the base material itself is the fluoropolymer polytetrafluoroethylene (PTFE). A preferred form of PTFE is tubing that has been stretched to create a uniform porous structure such as that taught in U.S. Pat. Nos. 3,953,566 and 3,962,153; which teachings are incorporated herein by reference.

The fluorine-containing polymer on the vascular graft surface is subjected to plasma treatment using a non-polymerizing gas. The gas selected must be capable of providing anionic groups on the fluoropolymer. Such gases are well known by those skilled in the art and can include, for example, oxygen, carbon dioxide, water, nitrous oxide, or mixtures of gases including such non-polymerizing gases. If desired, the apparatus used can be the same apparatus used to deposit a fluoropolymer coating and the treatment can take place immediately following the deposition of the fluoropolymer coating or at some later time. Apparatus suitable for plasma treatment are well known by those skilled in the art. For example, one apparatus suitable for use in the present invention is the apparatus shown and described in U.S. Pat. No. 4,632,842 or 4,718,907. The vascular graft, usually tubular in shape, is first placed into the plasma apparatus. A vacuum in the range of 0.02 to 0.1 mm Hg is then applied to remove undesirable gaseous components. The non-polymerizing gas, for example, oxygen, is then introduced by bleeding in gas at one end of the apparatus combined with pumping at the other end of the apparatus such that flow of the gas is maintained and internal pressure is maintained in the range of about 0.1 to 1.0 mm Hg. RF energy is then applied through electrodes in close proximity to the vascular graft and the deposited fluoropolymer coating. Energy inputs in the range of about 1 to 100 watts may be used for a duration of about 10 to 600 seconds on each portion of the vascular graft to be treated.

The resulting vascular graft material contains surface anionic groups available for bonding with various proteins. The protein to be applied is preferably an extracellular matrix protein which promotes endothelial cell attachment such as laminin or fibronectin or mixtures of such proteins. However, type I, type III or type IV collagen and other proteins such as fibrin, vitronectin, tenascin, basic fibroblast growth factor, and proteins containing the arginine-glycine-aspartic acid (RGD) sequence may also be useful in the present invention. The protein is bound to the anionic fluoropolymer surface by contacting a concentrated solution of the protein with the anionic surface for a period of time effective to provide a desired amount of the protein on the surface.

The resulting vascular graft can be implanted in the human body. Ingrowth of endogenous endothelial cells can then occur after implantation on the protein-modified surface. Preferably, the vascular graft is also seeded at the time of implantation with autologous endothelial cells. Although it will be recognized by those skilled in the art that there are many ways of accomplishing the bonding of the protein and cell seeding, the invention will be best described in detail with respect to those aspects according to the following example.

EXAMPLE

Woven polyethylene terephthalate vascular grafts precoated with plasma-deposited polytetrafluoroethylene substantially as disclosed in U.S. Pat. No. 4,632,842 were obtained from Atrium Medical Corporation, Hollis, N.H. The graft material was either plasma treated to produce anionic functional groups, plasma treated to produce cationic functional groups or received no additional plasma treatment. The material treated to produce anionic functional groups was treated by plasma discharge in the presence of oxygen by bleeding oxygen into a bell chamber at a pressure of 0.4 mm Hg and initiating a capacitive plasma at 50 watts for a period of one minute. The material treated to produce cationic functional groups was treated by plasma discharge in the presence of ammonia by bleeding anhydrous ammonia into a bell chamber at a pressure of 0.4 mm Hg and initiating a capacitive plasma at 50 watts for a period of three minutes. The presence of positively or negatively charged functional groups was confirmed by a visual measure of cationic and anionic dye binding with bromothymol blue (an anionic dye) and toluidine blue (a cationic dye). Graft materials were held for 10 minutes in a phosphate buffer (pH 7.0) containing either bromothymol blue or toluidine blue. Graft materials were rinsed in several changes of phosphate buffer (pH 7.0) and then air-dried. The results were as set forth in Table 1.

TABLE 1

| Dye Binding Of Vascular Graft Material | | | | |
|---|---|---|---|---|
| Sample | Treatment | Anionic Dye | Cationic Dye | Charge |
| 1 | None | − | − | Neutral |
| 2 | O₂ + PLASMA | − | + | Negative |
| 3 | NH₃ + PLASMA | + | − | Positive |

Fibronectin was isolated from a fibronectin- and fibrinogen-rich byproduct of human factor VIII production by sequential gelatin and heparin affinity chromatography. Laminin was isolated from the murine Engelbreth-Holmes-Swarm tumor and purified by Sephacryl S-300 chromatography. Laminin purified in this manner migrated as two distinct bands at 200 and 400 kilodaltons (KDa). These procedures are well known to those in the art and may be found in greater detail in Herbst, T. et al, Differential Effects of Laminin, Intact Type IV Collagen, and Specific Domains of Type IV Collagen on Endothelial Cell Adhesion and Migration, J. Cell Biol. 106:1365-1373, 1988 and Mooradian, D. L., et al, Transforming growth factor Beta-1 Binds to Immobilized Fibronectin, J. Cell Biochem. 41(4):189-200, 1989. In all instances, the purity of these isolated proteins was determined using the SDS-PAGE test for protein molecular weight.

The fibronectin and laminin were labeled with $^{125}$I using immobilized chloramine T iodination reagent (Iodo-bead TM, Pierce, Rockford, Ill.). Generally, the protein to be iodinated was combined in a sealed container with Na$^{125}$I and Iodo-beads followed by chromatographic separation of the iodinated protein. The radiolabeled proteins were analyzed by the SDS-PAGE test followed by autoradiography and were found to be intact.

Figure 2:
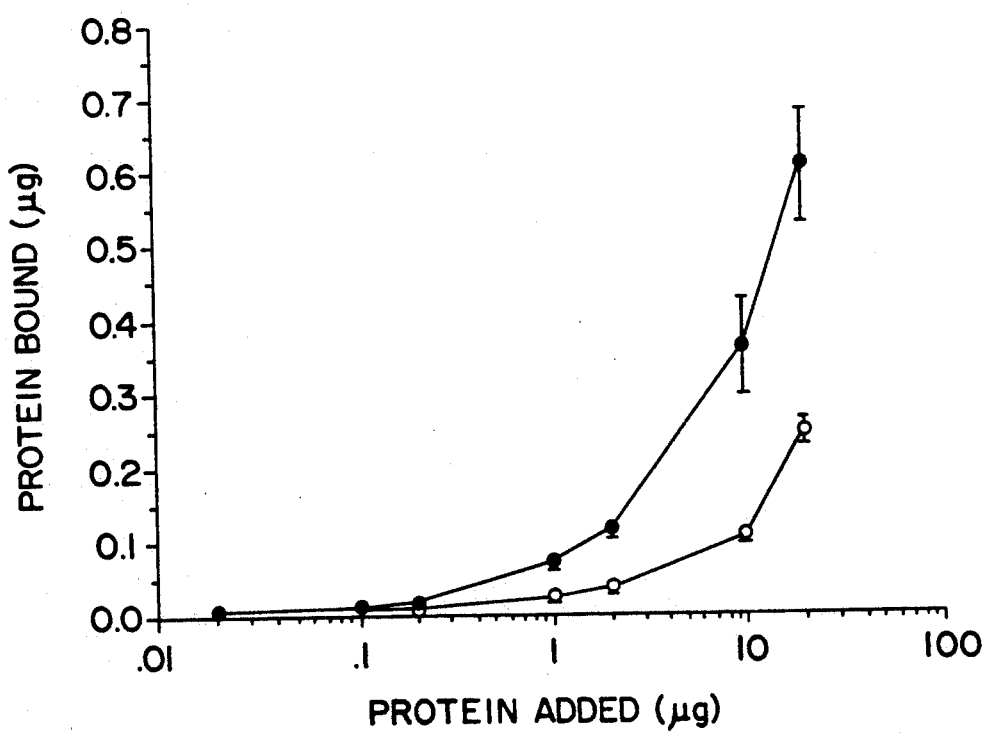
FIG. 2 is a graph showing concentration-dependent binding of laminin (solid data points) or fibronectin (open data points) to fluoropolymer deposited on vascular graft material according to the prior art.
Figure 3:
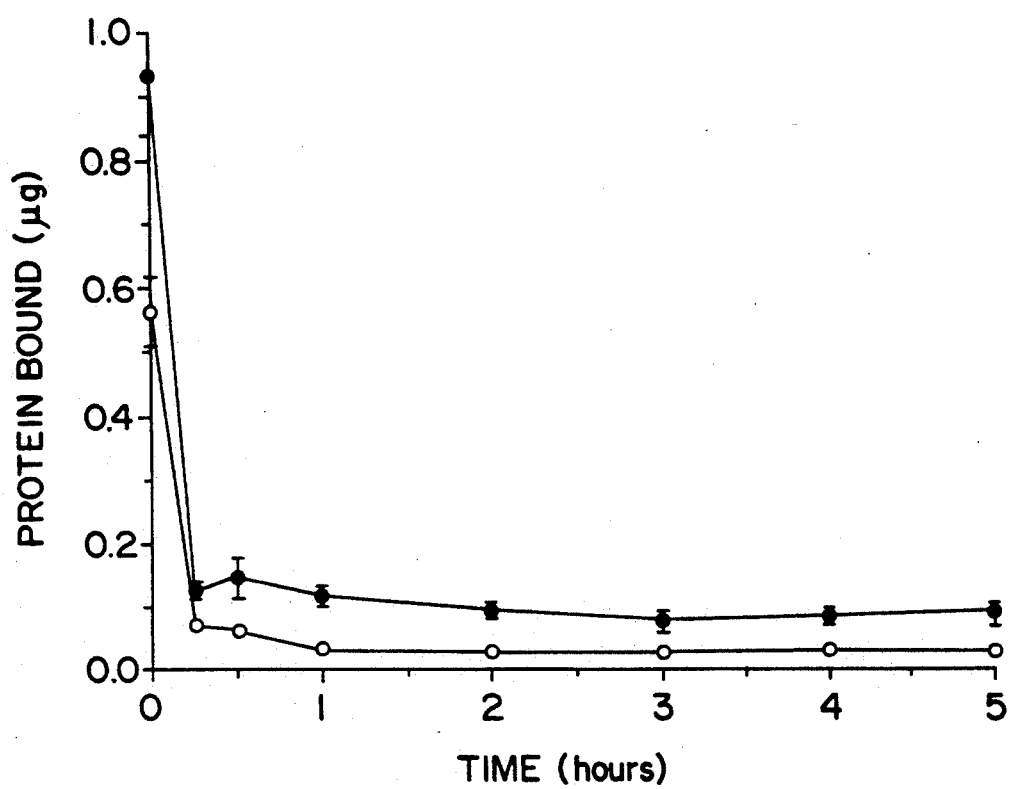
FIG. 3 is a graph showing time-dependent dissociation of fibronectin (open data points) and laminin (solid data points) from fluoropolymer deposited on vascular graft material according to the prior art.

To determine protein binding and retention, radiolabeled fibronectin or laminin were first applied to vascular graft material which received no additional plasma treatment. These test samples were not, therefore, made according to the present invention. Vascular grafts 10 mm in diameter were first cut to form a sheet and then cut into 6 mm discs. Proteins were then added to the discs in phosphate buffered saline (PBS) (pH 7.4) (100 μl.) containing 0.01% of a nonionic wetting agent (NP-40, Sigma Chemical Company, St. Louis, Mo.). Unbound protein was removed by washing the discs three times with the PBS solution (200 μl). The retention of radiolabeled laminin and fibronectin was determined by measuring radioactivity of the individual samples. As shown in FIG. 1, the binding of fibronectin and laminin was rapid and time-dependent, reaching a plateau after fifteen minutes. As shown in FIG. 2, the binding of these proteins was also dependent on protein concentration. As shown in FIG. 3, dissociation of both fibronectin and laminin from vascular graft material was also rapid, and only about 10% of the bound fibronectin and laminin was retained 60 minutes after washing.

Figure 4:
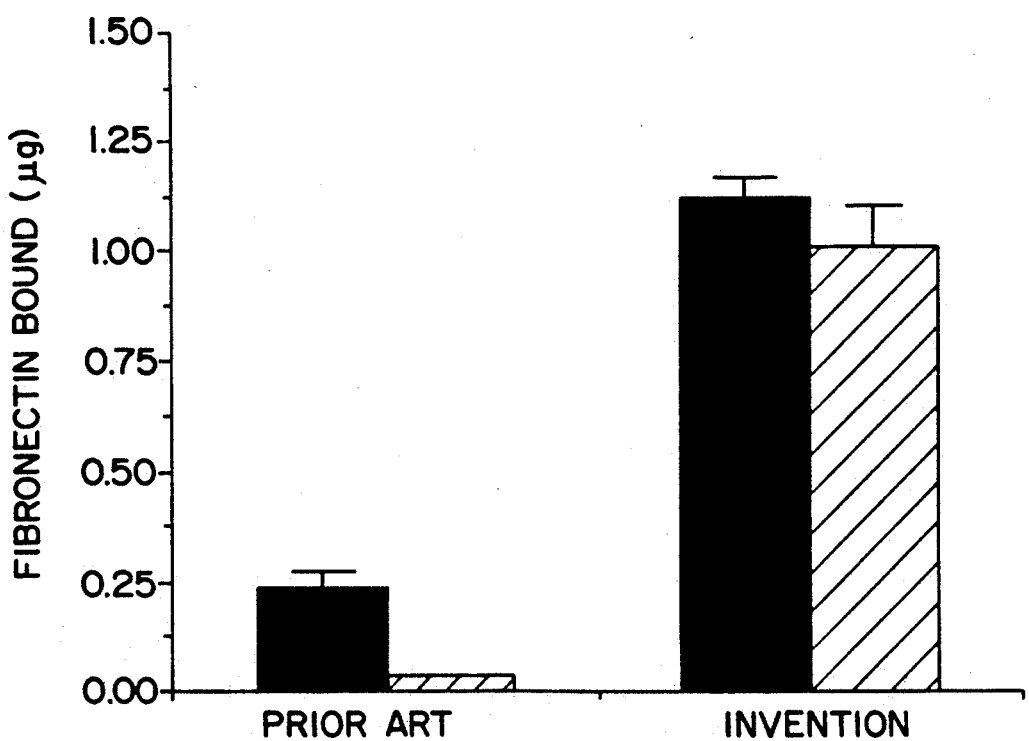
FIG. 4 is a bar graph comparing the binding of fibronectin to fluoropolymer deposited on vascular graft material according to the prior art and the binding of fibronectin to the plasma treated vascular graft material of the present invention. The total bound fibronectin and the amount remaining bound after one hour are shown.
Figure 5:
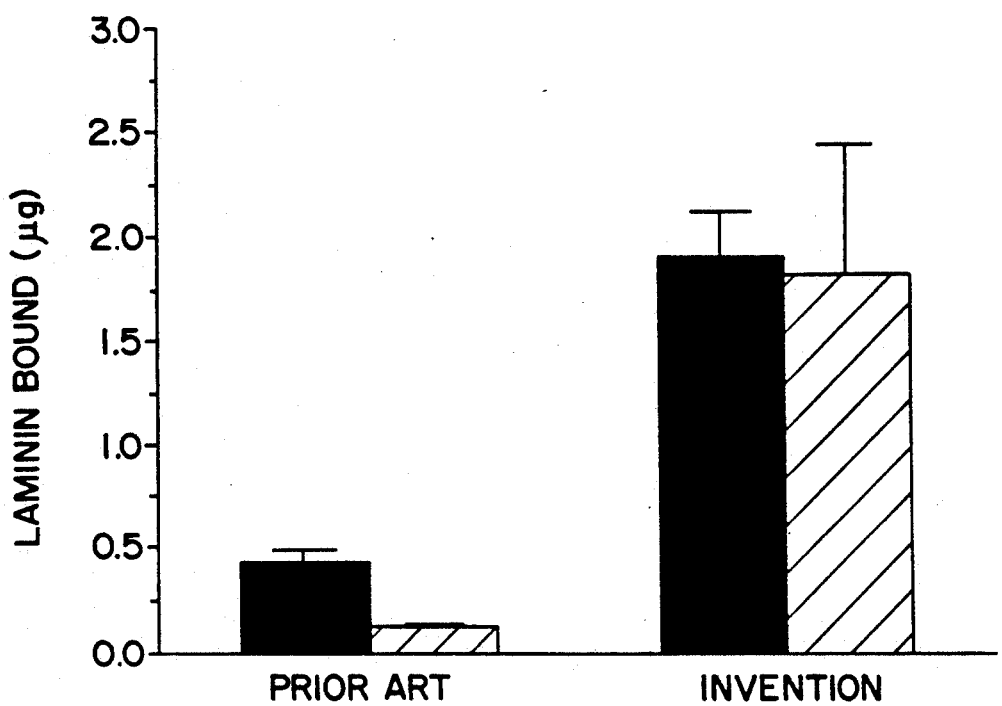
FIG. 5 is a bar graph comparing the binding of laminin to fluoropolymer deposited on vascular graft material according to the prior art and the binding of laminin to the plasma treated vascular graft material of the present invention. The total bound laminin and the amount remaining bound after one hour are shown.
Figure 6:
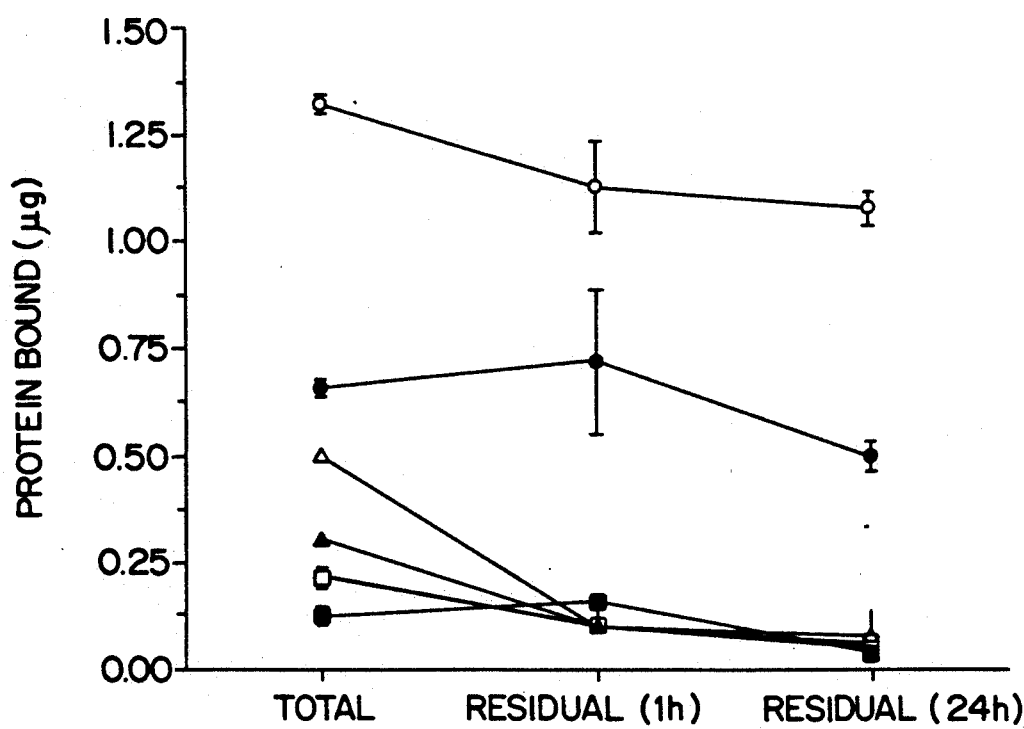
FIG. 6 is a graph comparing the retention of fibronectin and laminin to fluoropolymer deposited on vascular graft material and plasma treated according to the present invention (the first and second lines respectively) with the retention of fibronectin and laminin on fluoropolymer deposited on vascular graft material according to the prior art and also with the retention of fibronectin and laminin on fluoropolymer deposited on vascular graft material and plasma treated to make it cationic.

Similarly, samples were made employing vascular graft material that had been plasma treated to produce anionic functional groups (samples made according to the present invention), and also plasma treated to produce cationic functional groups. These samples were compared with samples of vascular graft material that had received no additional plasma treatment. As shown in FIG. 4, the binding of fibronectin to vascular graft material having a plasma treated anionic surface was approximately fivefold greater than the binding of fibronectin to the vascular graft material having no such treatment. Also, as shown in FIG. 4, after one hour the retention of bound fibronectin by the anionic vascular graft material was markedly greater than that of the untreated vascular graft material. Also, as shown in FIG. 5, the binding of laminin to vascular graft material having a plasma treated anionic surface was much greater than the binding of laminin to the vascular graft material having no such treatment. Also, as shown in FIG. 5, after one hour the retention of bound laminin by the anionic vascular graft material was markedly greater than that of the untreated vascular graft material. As shown in FIG. 6, retention over a 24 hour period was poor for untreated vascular graft material and no improvement was noted for vascular material which had been plasma treated to make it cationic but in the samples made according to the present invention, greater than 85% of the protein remained bound after 24 hours.

The effectiveness of the present invention for a cell seeding procedure was tested for vascular graft material that had been plasma treated to produce anionic functional groups (samples made according to the present invention), vascular graft material that had been plasma treated to produce cationic functional groups and vascular graft material that had received no additional plasma treatment. Endothelial cells were grown to 70-80% confluence in flasks and labeled with $^{35}$S-methionine for 24 hours. The cells were harvested using trypsin/EDTA, counted and resuspended in basal medium containing 2 mg/ml bovine serum albumin (BSA). Cells were seeded at 5,000 cells/disc onto the test samples of vascular prosthesis material precoated with fibronectin or laminin and cell adhesion was measured at regular time intervals. Cells were washed three times in defined medium containing 2 mg/ml BSA and then lysis buffer (1% SDS/0.5N NaOH) was added. Following lysis (30 minutes at 60° C.), the contents of each sample were transferred to a scintillation vial and measured on a scintillation counter. Endothelial cell adhesion to the untreated vascular graft material increased with time and 20-30% of the seeded endothelial cells adhered within 60 minutes. Results are shown in Table 2.

TABLE 2

| | | Endothelial Cell Adherence (%) | | |
|---|---|---|---|---|
| Sample | Treatment | No Protein | Fibronectin | Laminin |
| 1 | None | 26.3 | 34.0 | 26.0 |
| 2 | O$_2$ + PLASMA | 23.0 | 63.0 | 36.0 |
| 3 | NH$_3$ + PLASMA | 22.0 | 38.0 | 37.0 |

It should be evident to those skilled in the art that a variety of factors may influence the suitability of a particular adhesion-promoting protein for use as a substrate for autologous endothelial cell seeding. Such proteins can have a variety of effects on endothelial cell behavior in addition to their effects on cell adhesion. For example, proteins that promote cell adhesion may not promote cell spreading or cell migration. Cell spreading and cell migration may play an important role in the formation of stable functionally normal endothelial layer covering the luminal surface of the vascular graft following cell adhesion. Extracellular cell matrix proteins can also influence endothelial cell proliferation and endothelial cell proliferation may also play a role in attaining a completely endothelialized graft surface after seeding with limited numbers of autologous endothelial cells. The present invention is therefore not limited only to improvements in cell adhesion but extends also to the attachment of proteins that otherwise promote the formation of a stable, functionally normal endothelial cell layer covering the vascular graft after implantation in the human body.

While the invention has been described above in connection with particular embodiments and examples, one skilled in the art will appreciate that the invention is not necessarily so limited and that numerous other embodiments, examples, uses and modifications of and departures from the embodiments, examples nd uses may be made without departing from the inventive concepts.

We claim:

1. A method for making a vascular prosthesis comprising in sequence the steps of:
   a. plasma coating a vascular graft material with a fluoropolymer;
   b. separately treating the deposited fluoropolymer with a plasma in an atmosphere including only non-polymerizing gases and including at least one non-polymerizing gas capable of producing anionic groups; and c. binding a protein to the treated fluoropolymer.

2. The method of claim 1 further comprising the step of seeding endothelial cells onto the bound protein.

3. The method of claim 1 wherein the non-polymerizing gas is oxygen.

4. The method of claim 1 wherein the protein is selected from the group consisting of fibronectin, laminin, type I collagen, type III collagen and type IV collagen.

5. A vascular prosthesis made according to the method of any one of claims 1, 2, 3 or 4.

* * * * *